United States Patent
Ely et al.

(10) Patent No.: US 11,786,408 B2
(45) Date of Patent: Oct. 17, 2023

(54) PUSH-IN EARPLUG AND METHOD OF MAKING THE SAME USING A MANDREL

(71) Applicant: 3M INNOVATIVE PROPERTIES COMPANY, St. Paul, MN (US)

(72) Inventors: Jacob H. Ely, Carmel, IN (US); Robert C. Coffin, Plainfield, IN (US); James D. Brown, Bloomington, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/754,191

(22) PCT Filed: Sep. 24, 2020

(86) PCT No.: PCT/IB2020/058923
§ 371 (c)(1),
(2) Date: Mar. 25, 2022

(87) PCT Pub. No.: WO2021/059178
PCT Pub. Date: Apr. 1, 2021

(65) Prior Publication Data
US 2022/0296420 A1    Sep. 22, 2022

Related U.S. Application Data

(60) Provisional application No. 62/906,758, filed on Sep. 27, 2019.

(51) Int. Cl.
*A61F 11/08* (2006.01)
*B29C 44/12* (2006.01)
(Continued)

(52) U.S. Cl.
CPC ............ *A61F 11/085* (2022.01); *B29C 44/12* (2013.01); *B29C 44/1204* (2013.01);
(Continued)

(58) Field of Classification Search
CPC .................. B29C 44/1204; B29C 44/1228
See application file for complete search history.

(56) References Cited

U.S. PATENT DOCUMENTS

| 5,333,622 A * | 8/1994 | Casali ................ A61F 11/08 128/865 |
| 2003/0029459 A1 * | 2/2003 | Tiemens ................ B29C 48/06 128/864 |

(Continued)

FOREIGN PATENT DOCUMENTS

| JP | 04336235 | 11/1992 |
| WO | 2002062881 A2 | 8/2002 |

(Continued)

OTHER PUBLICATIONS

International Search Report for PCT International Application No. PCT/IB2020/058923, dated Dec. 17, 2020, 4 pages.

*Primary Examiner* — Kelly M Gambetta
*Assistant Examiner* — Virak Nguon
(74) *Attorney, Agent, or Firm* — Katherine M. Scholz

(57) ABSTRACT

A push-in earplug is provided. The push-in earplug comprises an elongate core comprising a core material. The push-in earplug also comprises an outer layer comprising a foam material, the outer layer covering at least a portion of an outer surface of the elongate core. The push-in earplug also comprises a channel extending through the elongate core from a first end of the elongate core to the second end of the elongate core.

20 Claims, 8 Drawing Sheets

(51) Int. Cl.
    *B29C 44/34* (2006.01)
    *B29C 48/00* (2019.01)
    *B29C 48/15* (2019.01)
    *B29C 44/56* (2006.01)
    *B29K 105/04* (2006.01)
    *B29K 27/18* (2006.01)
    *B29K 55/00* (2006.01)
    *B29K 77/00* (2006.01)

(52) U.S. Cl.
    CPC ...... *B29C 44/1228* (2013.01); *B29C 44/1271* (2013.01); *B29C 44/348* (2013.01); *B29C 44/3446* (2013.01); *B29C 44/3461* (2013.01); *B29C 44/5645* (2013.01); *B29C 48/0012* (2019.02); *B29C 48/15* (2019.02); *B29K 2027/18* (2013.01); *B29K 2055/00* (2013.01); *B29K 2077/00* (2013.01); *B29K 2105/04* (2013.01)

(56) References Cited

U.S. PATENT DOCUMENTS

| | | | |
|---|---|---|---|
| 2005/0039761 A1* | 2/2005 | Jenkins, Jr. | A61F 11/08 128/857 |
| 2006/0118124 A1 | 6/2006 | Woo | |
| 2008/0187161 A1* | 8/2008 | Tiemens | B29C 44/1214 264/275 |
| 2014/0017492 A1 | 1/2014 | Hamer | |
| 2014/0264995 A1* | 9/2014 | Lakshminarayanan | A61F 2/4455 264/642 |
| 2015/0335490 A1 | 11/2015 | Hamer | |
| 2017/0156933 A1* | 6/2017 | Hamer | B29C 44/1271 |

FOREIGN PATENT DOCUMENTS

| | | |
|---|---|---|
| WO | 2005018891 A1 | 3/2005 |
| WO | 2014011413 A2 | 1/2014 |
| WO | 2014126722 A1 | 8/2014 |

* cited by examiner

PUSH-IN EARPLUG AND METHOD OF MAKING THE SAME USING A MANDREL

CROSS REFERENCE TO RELATED APPLICATIONS

This application is a national stage filing under 35 U.S.C. 371 of PCT/IB2020/058923, filed Sep. 24, 2020, which claims the benefit of U.S. Provisional Application No. 62/906,758, filed Sep. 27, 2019, the disclosure of which is incorporated by reference in its/their entirety herein.

BACKGROUND

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-in type earplugs have also been considered, and may include a compressible attenuating portion and a stiff portion that extends from the attenuating portion. To insert a push-in type earplug, the user grasps the stiff portion and pushes the attenuating portion into the ear canal with an appropriate level of force. The attenuating portion compresses as it is accommodated in the ear canal. Push-in earplugs may allow the earplug to be quickly and easily inserted in an ear canal and may promote hygiene by minimizing contact with the attenuating portion of the earplug prior to insertion.

Although push-in earplugs exhibit desirable characteristics in various applications, they may be costly and may pose difficult manufacturing challenges.

SUMMARY

A push-in earplug is provided. The push-in earplug comprises an elongate core comprising a core material. The push-in earplug also comprises an outer layer comprising a foamable material, the outer layer covering at least a portion of an outer surface of the elongate core. The push-in earplug also comprises a channel extending through the elongate core from a first end of the elongate core to the second end of the elongate core.

DETAILED DESCRIPTION

"Mold" means a hollow form that may or may not impart a shape on a component placed in the hollow form.

"Thermally bonded" means a state in which molecules of two materials or surfaces have diffused into the material or surface of the other when in a molten phase such that a bond is formed. Chemical bonding is absent or does not provide the primary source of bonding between thermally bonded materials or surfaces.

"Thermoplastic" means a polymer that can be repeatably heated and re-shaped and will retain its shape upon cooling.

"Thermoset" means a polymer that may be irreversibly cured.

"Unactivated" when referring to a foaming agent means that the foaming agent can be further activated to facilitate the formation of gas or cells in a material.

Unless otherwise indicated, all percentages of compositions refer to percentage by weight.

An earplug that provides hearing protection for a user, and a method of making an earplug, is provided in the following description. Earplugs as described herein includes a relatively stiff elongate core covered, directly or indirectly, by a relatively soft outer layer. The outer layer includes a compressible sound attenuating portion that may be inserted into the ear canal of a user, and stem portion that may be grasped by a user to handle the earplug. Such an earplug may be easily inserted into an ear canal without first requiring that the sound attenuating portion be compressed or "rolled down."

Traditional earplugs are configured to entirely block an ear canal of a user, causing a relatively high level of attenuation. For environments where a lower amount of attenuation is needed or desired, a through-hole within the earplug reduces attenuation, specifically in the lower frequencies. Having a through-hole allows a consistent leak. Additionally, a through-hole can allow for incorporation of a filter or other acoustic device to produce a desired frequency response.

However, forming a through-hole within an earplug presents manufacturing difficulties because of the need to create the shaped sound attenuating portion that enters a user's ear.

Figure 1A:
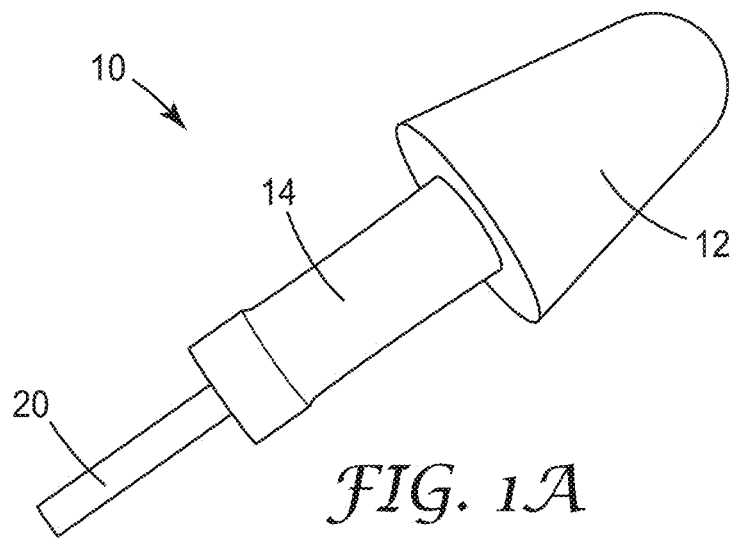
FIGS. 1A and 1B illustrate push-in earplugs according to an embodiment of the present invention.
Figure 1B:
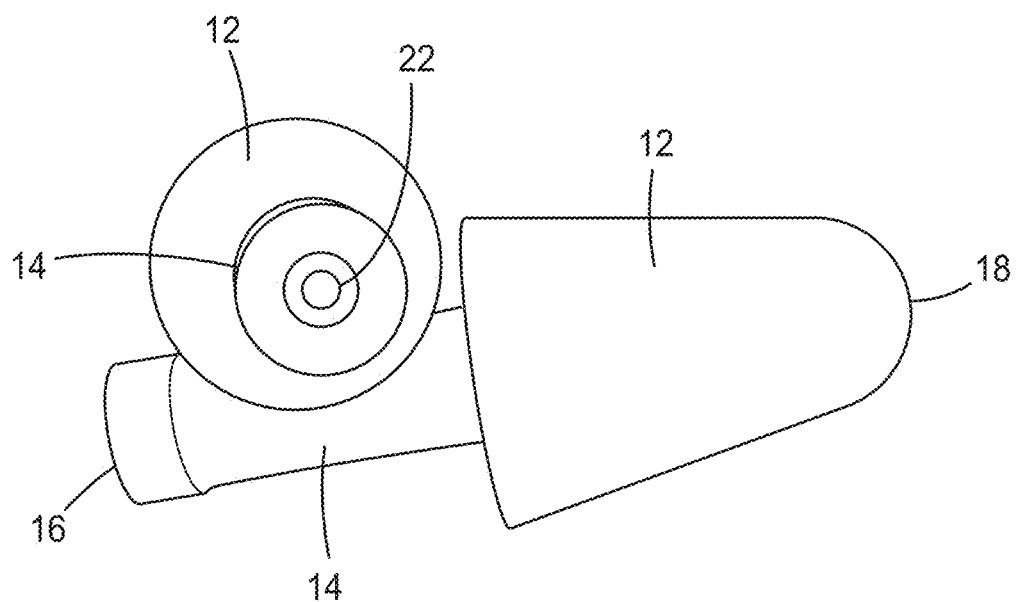

FIGS. 1A and 1B illustrate push-in earplugs according to an embodiment of the present invention. FIG. 1A illustrates a push-in earplug with a support structure, which may extend substantially from a first end to a second end of the earplug. The support structure is illustrated as partially removed to show how the features of the push-in earplug interact. In at least some embodiments, during manufacture, the support structure is substantially the same length as the length of an earplug preform, such that it does not extend beyond either end. In contrast, FIG. 1B illustrates a push-in earplug with a channel extending therethrough. The channel is formed by removal of the support structure.

FIG. 1A illustrates an earplug 10 during a manufacturing process. An earplug can be formed by layering a foamable overcoat over a semi-rigid plastic core. In one embodiment, the semi-rigid core surrounds a third inner layer, mandrel 20. Mandrel 20 is a different material than the inner core, and is designed to be removed after the foamable overcoat is activated to form stem portion 14 and sound attenuating portion 12. In one embodiment, mandrel 20 extends throughout earplug 10, from a first end 16 to a second end 18, illustrated in FIG. 1B, such that a channel 22 is formed extending through earplug 10.

Mandrel 20, in one embodiment, is made of a fluoropolymer. Fluoropolymers are advantageous materials for mandrel 20 as they are temperature stable enough to keep mandrel 20 from deforming during the high-temperature plug forming process. Additionally, a fluoropolymer mandrel 20 will also be temperature stable enough to allow mandrel 20 to be overcoated with the core material during an extrusion process without significant deformation. In some embodiments, when mandrel 20 is removed, the remaining channel 20 is substantially uniform in size along the length of earplug 10 from first end 16 to second end 18. Because mandrel 20 needs to be removable without significant deformation or tearing of earplug 10, it is also important that the material of mandrel 20 be substantially nonreactive with a core material. In one embodiment, mandrel 20 comprises polytetrafluoroethylene (PTFE). In another embodiment, mandrel 20 is fluorinated ethylene propylene (FEP).

It is also important that mandrel 20 be incorporated and removed without requiring the earplugs be mounted, for example, on an ejector pin. There are many uses for an earplug, such as earplug 10, with a channel 22 extending axially therethrough, such as low attenuation plugs and communication tips. Previous attempts to incorporate an axial channel have required first making hollow preforms, which had to be loaded onto ejector style pins in order to be supported during the molding process. Inserting a pin into each of the hollow preforms requires either significant manual effort or additional tooling. Use of mandrel 20 as a basis for earplug 10 allows for the creation of channel 22 without additional tooling or significant manual labor.

Figure 2:
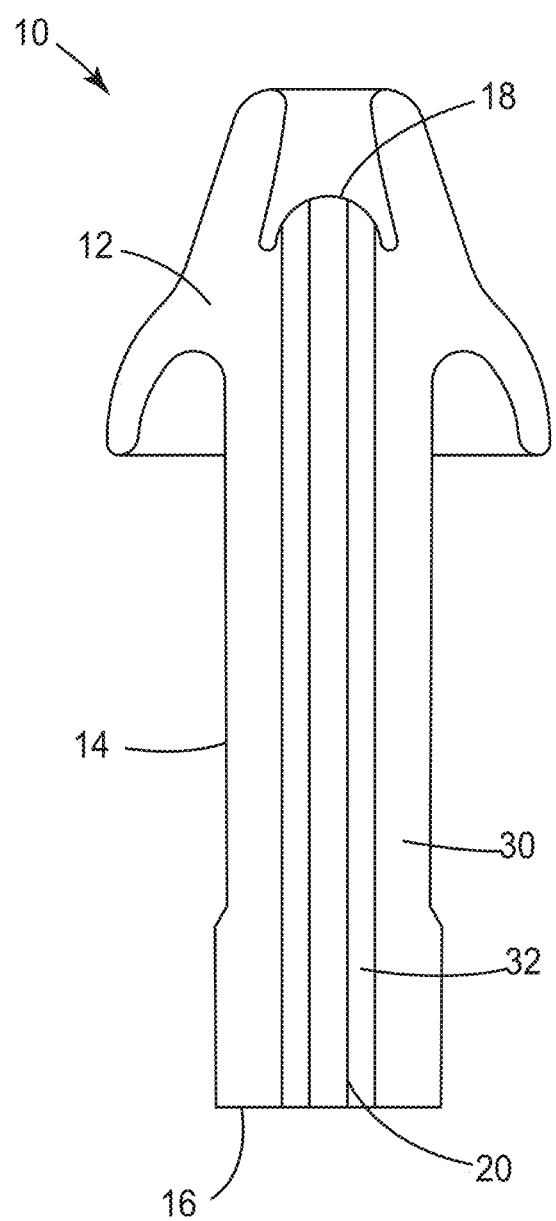
FIG. 2 is a cross-sectional view of a push-in earplug with a removable mandrel in an embodiment of the present invention.
Figure 3A:
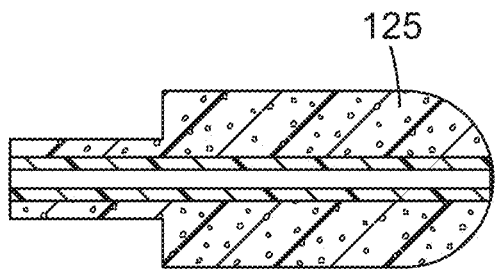
FIGS. 3A-3D are cross-sectional views of exemplary push-in earplugs according to the present invention showing sound attenuating portions having various exemplary shapes.
Figure 3B:
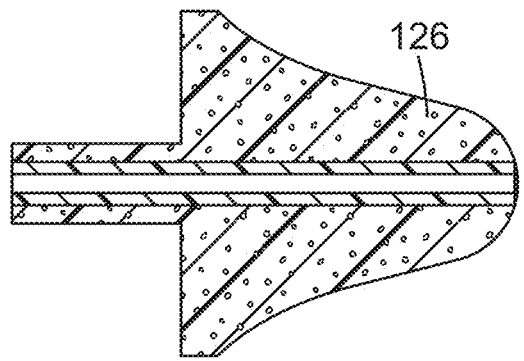
Figure 3C:
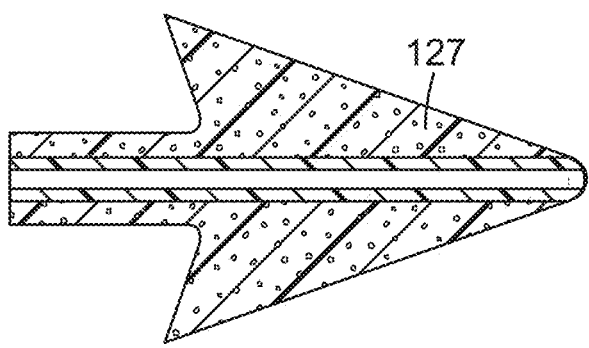
Figure 3D:
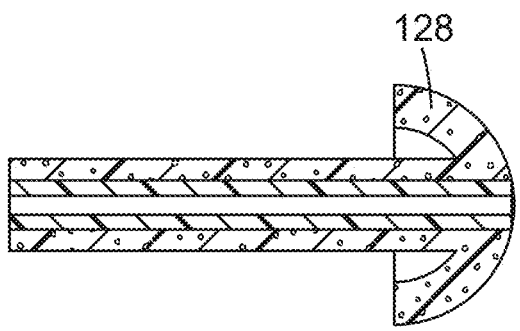

FIG. 2 is a cross-sectional view of a push-in earplug with a removable mandrel in an embodiment of the present invention. Earplug 10 is a push-in earplug having first and second ends 16 and 18, and an elongate core 32. Earplug 10 further includes an outer layer 30. Outer layer 30 includes a sound attenuating portion 12 for at least partial insertion into the ear canal of a user, for example, and a stem portion 14 having a smaller diameter and greater average density than sound attenuating portion 12.

During insertion of earplug 10, stem portion 14, supported by elongate core 32, serve as a handle which may be gripped by a user. Earplug 10, and specifically sound attenuating portion 12, is brought proximate to the user's ear and inserted into the ear canal. Sound attenuating portion 12 compresses as it is positioned, and elongate core 32 provides sufficient stiffness to facilitate insertion. In use, sound attenuating portion 12 is positioned substantially within an ear canal to block the passage of sound and stem portion 14 extends outwardly from the ear canal to provide a handle to remove the earplug. Outer, foamable layer 30 deforms to fit within the user's ear canal, allowing sound attenuation portion 12 to provide sound attenuation.

FIG. 2 illustrates a cross-sectional view of earplug 10 with a removable mandrel 20 extending from first end 16 to second end 18. Removable mandrel 20 is, in one embodiment, intended to be removed prior to sale of earplug 10 to a user. As illustrated, mandrel 20 remains substantially undeformed after foamable layer 30 undergoes a heat treatment and expands to form sound attenuating portion 12. Mandrel 20, in one embodiment, has a consistent cross-section along its length. In one embodiment, mandrel 20 forms the base of earplug 10 during manufacturing, such that core 32 is extruded over mandrel 20, and foamable layer 30 is then extruded over core 32. In one embodiment, mandrel has a cylindrical shape.

In one embodiment, elongate core 32 has a circular cross-section that is substantially uniform at any location between first and second ends 16 and 18 such that elongate core 32 exhibits a generally cylindrical shape. A circular cross section may minimize edges that may cause discomfort by contacting portions of a user's ear. In various other exemplary embodiments, elongate core may have a triangular, square, or other suitable cross-section, or may have a cross-section that varies along the length of earplug 10. The outer surface of earplug 10 may have a knurled, grooved, or otherwise textured surface, which may be formed simultaneously with foamable layer 30.

Earplug 10 further includes an outer layer 30 substantially covering, directly or indirectly, elongate core 32. Outer layer 30, in one embodiment, includes both a sound attenuating portion 12 and stem portion 14. In one embodiment, outer layer 30 substantially surrounds elongate core 32 and extends from first end 16 to second end 18 of elongate core 32. In some embodiments, outer layer 30 is a contiguous layer such that portions of sound attenuating portion 12 contact portions of stem portion 14. First and second ends 16 and 18 of elongate core 32 may be at least partially exposed, and elongate core 32 may be colored similarly or dissimilarly from the color of outer layer 30 to hide or exhibit the presence of elongate core 32.

Sound attenuating portion 12 is positioned near end 18 and is shaped to be accommodated in an ear canal of a user. In one embodiment, sound attenuating portion 12 has a bell-shape, and has a diameter at its widest point that is greater than a diameter of stem portion 14. In various other embodiments shown in FIGS. 3A through 3D, for example, sound attenuating portions 125, 126, 127, 128, respectively, may be bullet-shaped, hemispherical-shaped, cone-shaped, mushroom-shaped, or otherwise shaped to provide a desired fit or to suit a particular application.

Outer layer 30, as described in greater detail below, is formed of a material that is configured to, when heated, expand to fill a mold, allowing for the creation of a variety of shapes for sound attenuating portion 12.

The density of outer layer 30 can be controlled during manufacturing to provide a specified density as desired for a particular application. Outer layer 30 may exhibit a density that varies by thickness, for example, such that outer layer 30 has an integral outer skin that is more dense than the remainder of outer layer 30. Such a skin may be present on one or both of sound attenuating portion 12 and stem portion 14. Alternatively, sound attenuating portion 12 or stem portion 13 may have a substantially uniform density. In some embodiments, outer layer 30 is a foamable thermoplastic elastomer. The thermoplastic elastomer may be styrene-ethylene-butadiene-styrene (SEBS), a styrene-isoprene rubber (SIS), or a combination thereof.

Elongate core 32 provides a substrate which outer layer 30 may cover, directly or indirectly, and facilitates insertion of earplug 10 into the ear canal of a user. Elongate core 32 needs to have greater rigidity or stiffness than outer layer 30, but should be soft enough to be comfortable and safe for a user. Elongate core 32 should provide sufficient rigidity that earplug 10 may be positioned for use at least partially in the ear of a user by pushing sound attenuating portion 12 into the ear canal with an appropriate force. A sufficiently stiff elongate core 32, combined with an appropriate outer layer 30, will allow earplug 10 to be positioned at least partially in the ear of a user without the need to first compress or "roll down" sound attenuating portion 12. Direct insertion without the need to first compress or "roll down" sound attenuating portion 12, for example, promotes hygiene by limiting contact with sound attenuating portion 12 prior to placement in the ear. Elongate core 32 should also exhibit an appropriate level of flexibility such that it may slightly deform to the contours of the ear canal when positioned for use.

Previously, when manufacturing a hollow-core earplug, preforms would be mounted on steel pins during the molding process. If unsupported, hollow-core preforms collapse during the molding process. However, mounting each individual earplug onto a steel pin is a tedious manual process. It was desired to, instead, build a support system into the earplug preform assembly process. A channel forming feature can be used as the basis for extrusion and molding of an earplug. The channel forming feature needs to be removable after the molding process is complete. Therefore, the channel forming feature must be formed of a material that will not significantly deform during the molding process, and must be chemically inert with respect to a core layer of an earplug. This allows for removal of the channel forming feature after formation of the earplug without tearing or deformation, leaving a channel extending throughout the stem and sound attenuation portions of the earplug.

One important aspect of earplug design and construction, therefore is the selection of materials for mandrel 20, elongate core 32 and outer layer 30. During the manufacturing process, the foamable outer layer 30 will heat up and expand to fit the shape of a mold. At the same time, the foamable layer 30 will also thermally bond to core 32. This requires at least some miscibility with the thermoplastic elastomer. Mandrel 20, however, should not experience any thermal bonding to core 32, as mandrel 20 needs to be removable from core 32 without causing damage to core 32 and leaving a channel 22 extending throughout.

The core material should not melt or deform at the temperatures required for expansion of foamable overcoating layer 30. Additionally, it is desired that the core material have a tunable stiffness, such that the earplug is stiff enough for insertion into a user's ear, but still comfortable during use. In some embodiments, elongate core 32 comprises a blend of materials. However, elongate core 32 may also comprise a single material. In one embodiment, core 32 and outer layer 30 are the same material, such that only a mandrel and a earplug material are selected.

The mandrel needs to have high temperature resistance to withstand the heat applied during the molding process without significant deformation. It also needs to be removable from the earplug, once formed. In one embodiment, the mandrel is a fluoropolymer, such as PTFE or FEP. However, while PTFE and FEP are suitable materials, others may also be possible. A material that is substantially chemically inert with respect to the earplug core material, and has a melting temperature above 190° C. might also be suitable.

In one embodiment, core 32 comprises about a 65% polyamide mixture and about 35% polypropylene, measured by weight. The polyamide mixture comprises an impact modifier. The impact modifier is at least 10% or at least 15% or at least 20% or at least 25% of the polyamide mixture, measured by weight. In one embodiment, the impact modifier is maleated styrene-ethylene-butylene-styrene (SEBS). Inclusion of an impact modifier surprisingly resulted in an improved flexibility without significant reduction in core stability. However, while one particular core material composition is described, it is also envisioned that other embodiments may have other core materials.

FIGS. 3A-3D are cross-sectional views of exemplary push-in earplugs according to the present invention showing sound attenuating portions having various exemplary shapes. While FIG. 1 illustrates one example shape of a sound attenuating portion of a push-in earplugs, other embodiments are shaped differently. For example, any of sound attenuating portion shapes 125, 126, 127 or 128 may be possible. Other suitable shapes are also envisioned.

Figure 4:
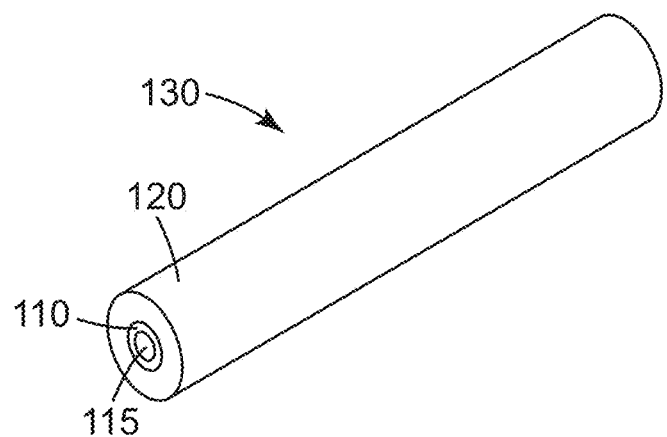
FIG. 4 is a perspective view of an earplug pre-form in an intermediate state of an exemplary method of making an earplug.

FIG. 4 is a perspective view of a pre-form that includes an elongate core and an outer layer in an intermediate state of one method of making an earplug. An earplug may be formed in a multiple step process. In one embodiment, the earplug is formed in a process that involves coating a mandrel 115 with a core material 110, and then coating the core material 110 with an outer layer 120 is covered around elongate core 110, directly or indirectly, to result in a pre-formed hearing protection device such as pre-form 130.

In the intermediate state shown in FIG. 4, outer layer 120 of pre-form 130 includes an unactivated foaming agent. In one embodiment, the unactivated foaming agent includes an expandable sphere foaming agent that includes thermoplastic spheres, for example, that include a shell encapsulating a hydrocarbon or other appropriate gas that expands when exposed to heat or other activation source. Expansion of the thermoplastic shell results in an increased volume and reduced density of the material of outer layer 120. The unactivated foaming agent may also be a chemical foaming agent that includes an expandable material that is self-contained or otherwise not contained by an expandable sphere. Activation of such a foaming agent causes the expandable material to expand, creating voids or gaps in the material of the outer layer. In one embodiment, outer layer 120 of pre-form 130 includes an unactivated expandable sphere foaming agent and an unactivated chemical foaming agent. Activation of the foaming agent or agents present in outer layer 120, and the associated expansion of outer layer 120, can be controlled to provide an earplug 10 having a sound attenuating portion 12 and stem portion 14 exhibiting a desired shape, density, hardness, and other desired characteristics.

The presence of both an expandable sphere foaming agent and a chemical foaming agent may assist in providing sufficient structure and expansion such that outer layer 120 may be appropriately formed during activation, while reducing the hardness of outer layer 120 from a level that would otherwise result if only an expandable sphere foaming agent were used. Some or all of a gas generated by a chemical foaming agent may escape during activation such that some or all of the gas is not present in the outer layer after activation. Some or all of an expandable sphere foaming agent may remain in the outer layer of a final earplug such that a final earplug may include thermoplastic spheres. In one embodiment, outer layer 120 of earplug 100 includes between 1% and 5% weight, and may include approximately 3% weight, of the foaming agent or remnants of the foaming agent.

In the intermediate state shown in FIG. 4, pre-form 130 may be cut to the desired length of earplug 100, may be cut to an extended length sufficient for subsequent formation of many earplugs.

Figure 5:
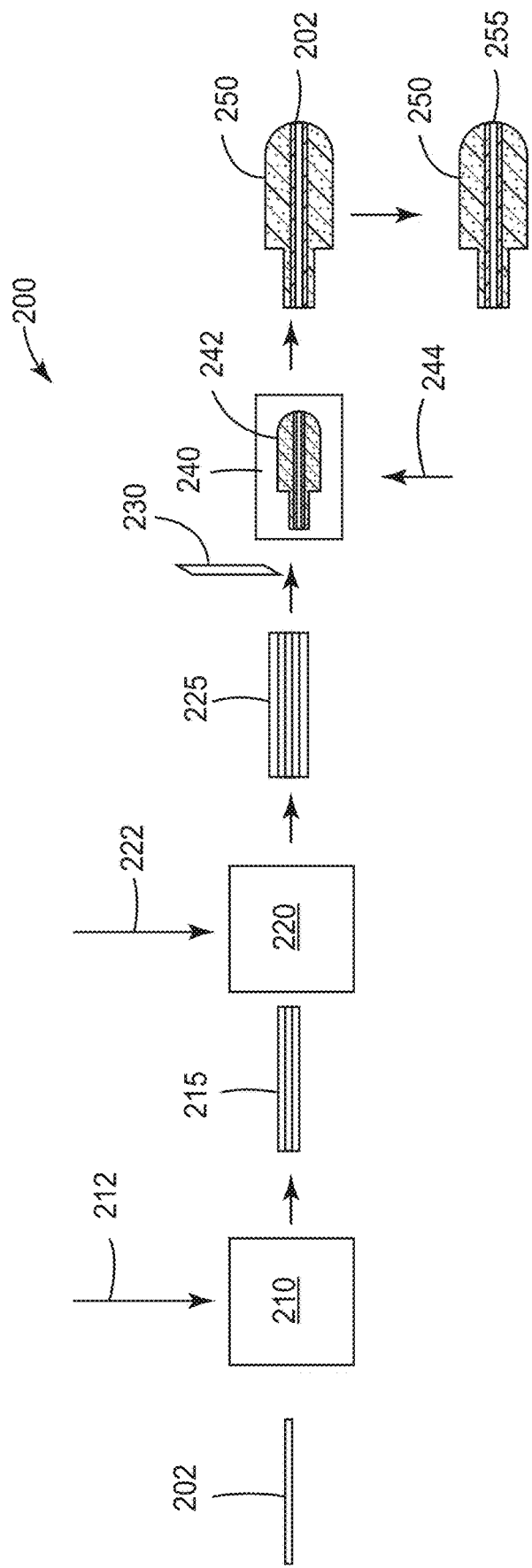
FIG. 5 is a schematic representation of an exemplary manufacturing process according to the present invention.

FIG. 5 is a schematic representation of one manufacturing process according to the present invention. The present invention further provides a method of making an earplug. The method may include the steps of covering a mandrel, or other supporting structure, with an earplug core material such as a blended polymeric material. The core material is then covered with an additional outer layer that includes an unactivated foaming agent. The manufacturing process then includes activating the foaming agent such that at least a portion of the outer layer expands into a desired shape. Components of schematic 200 are not drawn to scale.

A mandrel 202 is provided to a first extruder 210 along with core material 212. Extruder 210 outputs an extruded elongate core 215, which includes mandrel 202 substantially covered by core material 212.

Mandrel 202 has the shape of a desired internal channel 255 of earplug 250. Mandrel 202 may be cylindrical, as depicted herein. However, other shapes may be suitable for other embodiments. For example, a rectangular prism, triangular prism, or another suitable shape may also be used, depending on the function of channel 255.

Core material 212, in one embodiment, comprises a polyolefin. In one embodiment, core material 212 comprises an impact modifier. In one embodiment, core material 212 comprises at least about 50% polyamide, or at least about 60% polyamide. In one embodiment, core material 212 comprises at least about 65% polyamide mixture and at least about 35% polypropylene. The polyamide mixture, in one embodiment, comprises at least 10% impact modifier, or at least 15% impact modifier, or at least 20% impact modifier, or at least 25% impact modifier. In one embodiment, the impact modifier is SEBS.

Elongate core 215, along with a second material 222, is provided to a second extruder 222, which outputs a preform 225. Preform 225 includes elongate core with an overlayer formed from the second material. Second material 222 may comprise a foamable material. Extruders 210 and 220 co-extrusion dies or other suitable die as known in the art.

In one embodiment, the foamable material comprises a thermoplastic and one or more unactivated foaming agents. Second material is applied to elongate core 215 while remaining at a temperature below an activation temperature of the unactivated foaming agents. In one embodiment, second material includes styrene-ethylene-butylene-styrene (SEBS) and a foaming agent having an activation temperature between 100° C. and about 205° C., or between 120° C. and about 190° C., or of about 170° C. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art. In embodiments in which second material 222 includes a rubber or thermoset polymer, second material 222 may be applied at a temperature below a vulcanizing or curing temperature of the rubber or thermoset polymer. In such an embodiment, second material may include an unactivated foaming agent and an uncured or partially cured rubber or thermoset polymer that can be subsequently activated and cured, respectively, with heat or other suitable activation or curing process.

The weight percentage of a foaming agent in second material 222 when initially applied to blended elongate core 215 may be selected based on the type of thermoplastic or other material used and the desired final shape, density, hardness or other characteristics of a sound attenuating portion. In one embodiment, second material 222 has an initial composition of between 90% and 99.5% SEBS and between 10% and 0.5% of an appropriate unactivated foaming agent, or of approximately 93% SEBS and 7% of an unactivated expandable sphere foaming agent, such as EXPANCEL 930 DU 120, EXPANCEL 920 DU 120, both available from Eka Chemicals AB of Sundsvall, Sweden.

In other embodiments, second material 222 has an initial composition including an unactivated chemical foaming agent such as oxybis benzene sulfonyl hydrazide (OBSH) available from Biddle Sawyer Corp. of New York, N.Y. The presence of a chemical foaming agent such as an OBSH foaming agent may yield a sound attenuating portion having a lower hardness value than a sound attenuating portion formed by including an expandable sphere foaming agent such as EXPANCEL as the only foaming agent.

In one embodiment, second material 222 includes an unactivated expandable sphere foaming agent and an unactivated chemical foaming agent. The presence of both an expandable sphere foaming agent and a chemical foaming agent may assist in providing sufficient structure such that the outer layer may be appropriately formed and that may not be present with a chemical foaming agent alone, while reducing the hardness of the outer layer from a level that would otherwise result if only an expandable sphere foaming agent were used. Accordingly, the combination of a chemical foaming agent and an expandable sphere foaming agent may result in an outer layer having a hardness level appropriate for a desired application, such as for insertion into an ear canal. In one embodiment, second material when initially applied may include between approximately 0.5% weight and 3% weight of an unactivated chemical foaming agent, or of approximately 2% weight of an unactivated chemical foaming agent, and between approximately 0.5% weight and 9.5% weight of an unactivated expandable sphere foaming agent, or of approximately 2% weight of an unactivated expandable sphere foaming agent. Second material 222 may also include other suitable foaming agents, or various combinations of EXPANCEL foaming agents, OBSH foaming agents, and other suitable foaming agents. Second material 222 may further include pigment to impart a desired color, antioxidants, UV stabilizers, and oils or waxes to aid in extrusion and mold release as known in the art.

In some exemplary embodiments, second material 222 is in a molten state when covered over elongate core 215. As a result, molecules of second material 222 and elongate core 215 or of one or more intermediate layers, are believed to diffuse into the material or surface of each other and a thermal bond is formed. When the materials or surfaces cool and solidify to form preform 225, the outer layer remains thermally bonded, directly or indirectly, to elongate core 215. In one embodiment, significant chemical bonding is absent such that the primary source of bonding between layers of preform 225 is thermal bonding. In other exemplary embodiments, there is substantially no bonding between layers of preform 225. However, in some embodiments, upon activation and/or curing during molding of a sound attenuation portion, a thermal bond may be formed, directly or indirectly, between the layers of preform 225.

In other exemplary embodiments, elongate core 215 may be covered with second material 22 by laminating, molding, spraying, dipping, or other suitable process as known in the art as an alternative or in addition to second extruder 220. Regardless of the process used, the temperature of second material 222 should remain below the activation temperature of the foaming agent(s) such that the foaming agent(s) remain unactivated during the covering process. In the event that an uncured or partially cured material is included in second material 222, such as an EPDM rubber or thermoset polymer, the temperature of second material 222 should remain below the curing temperature.

While only two material layers 212, 222 are described, it is expressly contemplated that similar methods could be applied for a third, fourth, or even more materials. Additionally, while applicators 210, 220 are described as extruders, other application technologies are also expressly contemplated.

In one embodiment, preform 225 is cut to the length of a desired earplug with cutter 230 prior to a molding process. Cutter 230 may cut pre-form 225 to a desired length of earplug 250, or to an extended length sufficient for subsequent formation of many earplugs. In one embodiment, pre-form 225 is cut to an extended length that can be subsequently cut and activated, or vice versa, to yield a desired quantity of earplugs 250. An extended pre-form 225 may be coiled or otherwise shaped for ease of handling or transportation. While cutter 230 is described as a separate manufacturing step, it is also contemplated that it may be part of extruder 220. Additionally, cutter 230 may be part of extruder 210 in another embodiment.

Preform 225 is provided to a mold cavity 242 within a mold 240. Heat 244, or another activation mechanism, is applied, causing the foamable over layer to expand within, and conform to the shape of, mold cavity 242. Once the activation process is complete, an earplug 250 is removed from mold 240. A channel 255 is formed by removing mandrel 202. The mandrel can be removed, in one embodiment, by applying a force to one end, for example either pushing or pulling mandrel 202 out of the core.

Core 215 and preform 225 may be cooled in between extrusion and/or cutting operations. Illustrated in FIG. 5 is an embodiment where the entirety of preform 225 is placed within mold cavity 242. However, in some embodiments only a portion of preform 225, the sound-attenuating portion for example, is placed into the mold. In one embodiment, the foaming agent is activated by heat or other activation source to cause the outer layer of preform 225 to expand. In some embodiments in which the outer layer includes an uncured or partially cured material, application of heat or other activation source also causes the outer layer to cure. In one embodiment, mold cavity 242 includes a first cavity in the form of a stem portion and a second cavity in the form of a sound attenuating portion. Upon application of heat or other suitable activation source, a portion of the outer layer expands to fill the second cavity and substantially conform to the shape of second cavity, while the portion positioned in the first cavity is effectively shielded from heat such that activation of the foaming agent is limited. Alternatively, or in addition, expansion of the outer layer that would otherwise occur during activation of the foaming agent is substantially constrained by the shape of the first cavity. In one embodiment, mold 240 includes small gas vents to allow excess gas to escape while preventing passage of any molten material.

In another exemplary embodiment, only a portion of preform 225 is positioned in a mold cavity. The mold cavity may be in the form of a stem such that expansion of a portion of preform 225 is substantially constrained to form a stem, while the remaining portion of preform may freely expand to form a sound attenuating portion. Alternatively, the mold cavity may be in the form of a sound attenuating portion such that expansion of a portion of preform is constrained and selectively activated to form the sound attenuating portion, while the remaining portion of preform 225 is not activated, or is only partially activated, and forms a stem.

Figure 6A:
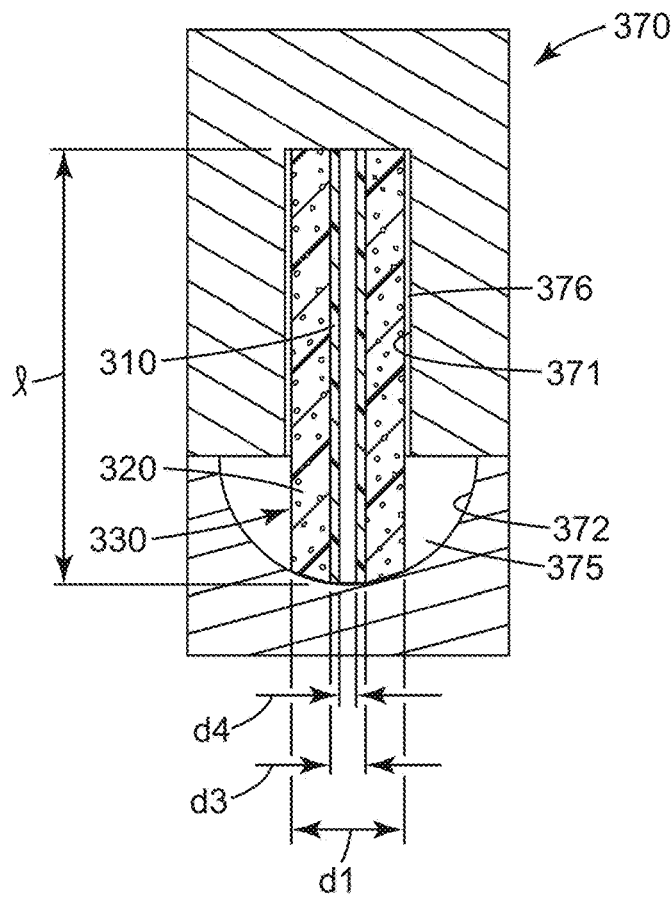
FIGS. 6A and 6B are cross-sectional views of an earplug preform in a mold in an exemplary embodiment of the present invention.
Figure 6B:
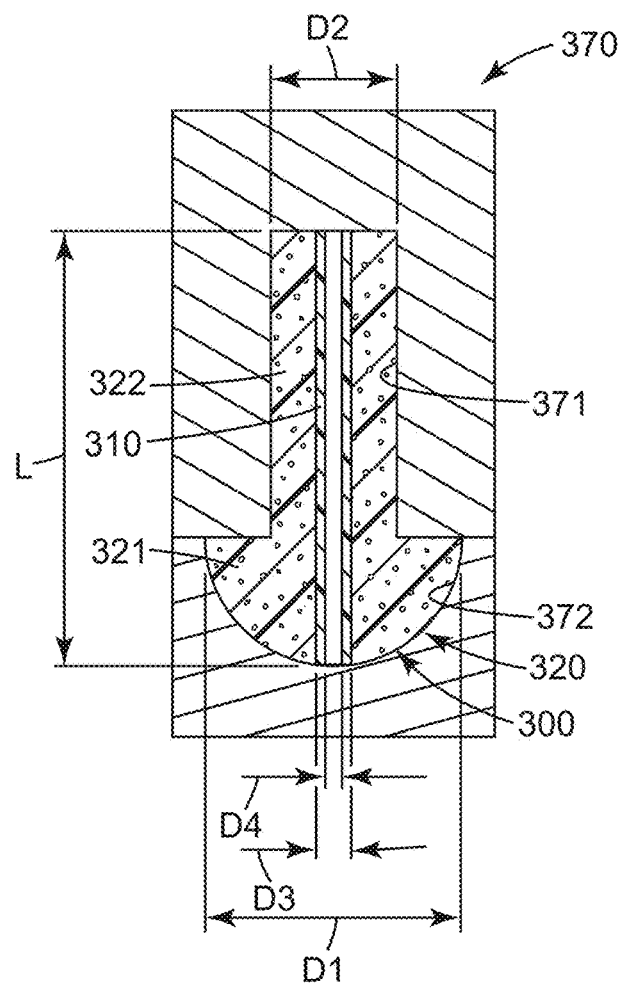

In the exemplary embodiment of FIGS. 6A and 6B, mold 370 is used to control expansion of outer layer 320 of pre-form 330. Mold 370 includes a first cavity 371 in the form of a stem portion that receives a portion of pre-form 330. Mold 370 further includes a second cavity 372 in the form of a sound attenuating portion. When pre-form 330 is initially placed in mold 370, a gap 375 exists between pre-form 330 and a perimeter of second cavity 372. In some embodiments, a small gap 376 may exist between pre-form 330 and a perimeter of first cavity 371. Upon application of heat or other suitable activation source, a portion of outer layer 320 expands to fill gap 375 and substantially conforms to the shape of second cavity 372. The portion of earplug 300 positioned in first cavity 371 may be effectively shielded from heat such that activation of the foaming agent is limited. Alternatively or in addition, expansion of outer layer 320 that would otherwise occur during activation of the foaming agent is constrained by first cavity 371. Further, as application of heat softens outer layer 320 and the foaming agent is activated, outer layer 320 may expand to fill first cavity 371 and some of outer layer 320 initially in first cavity 371 may flow into second cavity 372 to fill gap 375. In one embodiment, mold 370 includes small gas vents to allow excess gas to escape while preventing passage of any molten material.

In one embodiment, mold 370 is oriented such that first cavity 371 is oriented above second cavity 372 during a portion or all of the activation process. Such an orientation may allow material to flow from first cavity 371 into second cavity 372 during activation. Further, an orientation in which first cavity 371 is oriented above second cavity 372 may facilitate the formation of an integral skin on sound attenuating portion 321 because cells or gaps formed during activation of the foaming agent may tend to move upward and away from a lower surface of cavity 372.

Earplug 300 is subsequently cooled and ejected from mold 370. Finished earplug 300 includes a sound attenuating portion 321 having the shape of second cavity 372 of mold 370, and a stem portion 322 having the shape of first cavity 371 of mold 370. Due to the constraint of first cavity 371 and/or limited activation of the foaming agent in the area of first cavity 371, stem portion 322 may have a greater average density and/or hardness than that of sound attenuating portion 321.

In the exemplary embodiment shown in FIGS. 6A and 6B, earplug 300 is formed from pre-form 330 having a total length l in a longitudinal direction between approximately 15 mm and 40 mm, or of about 25.5 mm. Outer layer 320 has an outer diameter dl between approximately 2.5 mm and 6.5 mm, or of about 4.5 mm, elongate core 310 has an outer diameter d3 between approximately 1.5 mm and 3.5 mm, or of about 2.5 mm, and channel 315 has a diameter d4 between approximately 1.0 mm and 2.0 mm or of approximately 1.5 mm. After activation of outer layer 320 described above, as shown in FIG. 6B, final earplug 300 has a total length L in a longitudinal direction between approximately 15 mm and 40 mm, or of approximately 25.5 mm, sound attenuating portion 321 has an outer diameter D1 at its widest point between approximately 8 mm and 16 mm, or of approximately 12.5 mm, stem portion 322 has a diameter D2 between approximately 3 mm and 10 mm, or of approximately 6.5 mm, elongate core 310 has an outer diameter D3 between approximately 1.5 mm and 3.5 mm, or of approximately 2.5 mm, and channel 315 has a diameter D4 between approximately 1.0 mm and 2.0 mm, or of approximately 1.5 mm. The dimensions of pre-form 330 and finished earplug 300 can be varied based on the materials of outer layer 320 and elongate core 310, and as required to form a final earplug 300 having desired characteristics for a particular application.

Figure 7B:
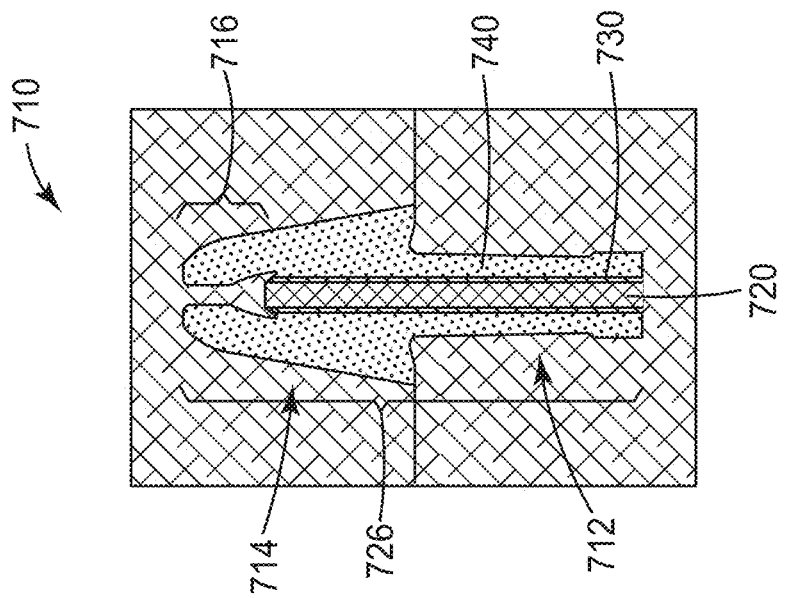
FIGS. 7A and 7B are cross-sectional views of an example of a mold and formed earplug in an exemplary embodiment of the present invention.
Figure 7A:
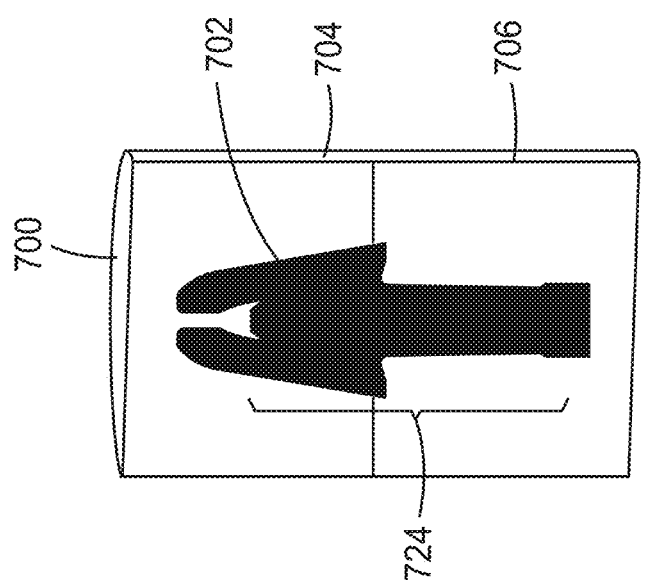

FIGS. 7A and 7B are cross-sectional views of an example of a mold and formed earplug in an exemplary embodiment of the present invention. Mold 700 has a cavity 702, formed of a sound attenuating cavity portion 704 and a stem cavity portion 706. Mold 700 is used to control expansion of an outer layer 740. Stem cavity portion 706 that receives a portion of an earplug preform. Heat is applied to raise the temperature of outer layer 440 at least to an activation temperature of a foaming agent and cause outer layer 740 to expand, filling mold cavity 702 as shown in FIG. 7B. In one embodiment, the portion of the earplug positioned in stem cavity portion 706, may be effectively shielded from heat such that activation of the foaming agent is limited. Alternatively or in addition, stem cavity portion 706 constrains outer layer 740 and substantially inhibits expansion caused by activation of the foaming agent that would otherwise result in a greater volume and less dense outer layer.

A finished earplug 710 includes a sound attenuating portion 714 formed by the exposed outer layer that could freely expand and a stem portion 712 that was at least partially constrained in mold 700 during activation of the foaming agent. Due to the constraint of the mold and/or limited activation of the foaming agent, stem portion 712 may have a greater average density and/or a greater hardness than that of sound attenuating portion 714.

As illustrated in FIG. 7B, in some embodiments, mandrel 720 and elongate core material 730 do not extend completely throughout the length of an earplug 710. Because elongate core 730 has a higher stiffness, an earplug 710 may be more comfortable if only expanded outer layer 740 is present for portion 716, which is insert innermost into a user's ear. Portion 716 forms a cavity that is shaped to provide comfort to a user wearing earplug 710. Therefore, in some embodiments, a post-mold length 726 of an earplug may be greater than a pre-mold length 724. In one embodiment, portion 716 is about 0.2 inches long. The length of an overall preform may be at least about 0.75 inches, or at least about 0.80 inches, or at least about 0.90 inches, or at least about 1.00 inches. In one embodiment, a length of mandrel 720 and a length of core material 730 are about the same.

Figure 8:
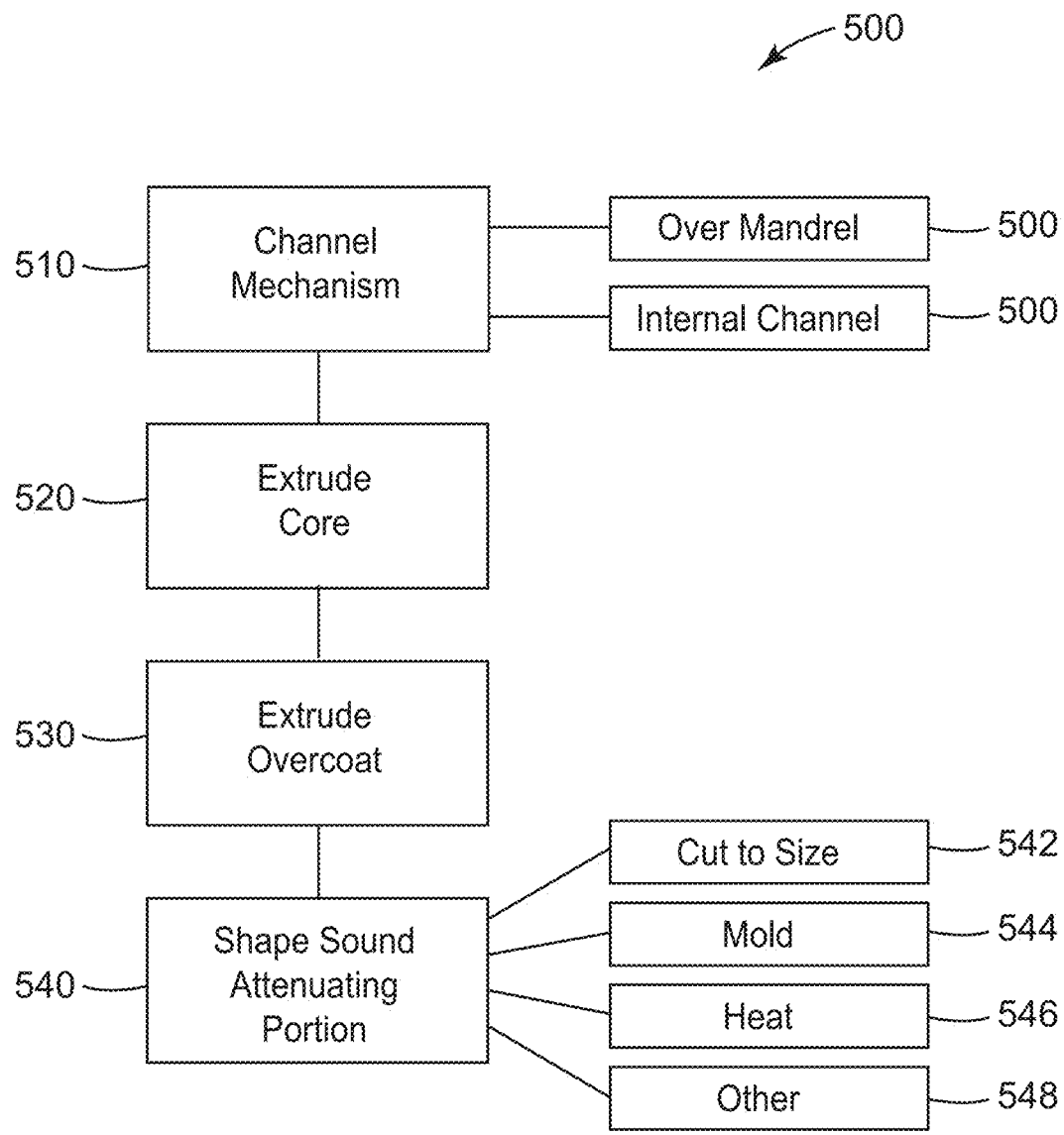
FIG. 8 illustrates an exemplary schematic for manufacturing an earplug in accordance with embodiments of the present invention.

FIG. 8 is a method of manufacturing a push-in earplug in an exemplary embodiment of the present invention. Method 500 may be useful for forming any of the in-ear plugs described herein, as well as other suitable ear plugs with channels therethrough. Method 500 may be performed using a system similar to the schematic described with respect to FIG. 5 or using another suitable system.

In step 510, a channel mechanism is selected. The channel mechanism may be a mandrel, as indicated in block 502. The mandrel may be cylindrical in shape, with the dimensions of a desired channel in the manufactured earplug. However, in another embodiment, a channel is created by selecting a material for an earplug core that can be extruded with a channel extending therethrough, and can maintain the extruded channel without significant deformation during the sound attenuation molding process, as indicated in block 504. Other channel mechanisms may also be suitable for other. For example, a channel mechanism may have oval shaped cross-section, or another suitable shape, depending on the use of a final earplug.

In step 520, a core is extruded over the channel mechanism.

In step 530, an overcoat layer is extruded over the core. In one embodiment, the overcoat layer substantially covers the elongate core. The overcoat layer is formed of a material that is configured to, when heated, expand to fill a mold cavity. The material may be selected to control the friability of the outer layer, such that it is not easily broken and does not disintegrate during use. The friability of an earplug may be controlled in part by selecting a material having an appropriate molecular weight, with higher molecular weight generally resulting in a less friable earplug. In some embodiments, the overcoat layer is a foamable thermoplastic elastomer. The thermoplastic elastomer may be styrene-ethylene-butadiene-styrene (SEBS), a styrene-isoprene rubber (SIS), or a combination thereof.

In step 540, a sound attenuating portion is formed. This may comprise cutting the coated mandrel down to size, as indicated in block 542. The sound attenuating portion may be formed by placing at least a portion of the coated core in a mold, as indicated in block 544. The mold may include a cavity with the desired shape of a sound attenuating portion, such as the shapes illustrated in FIGS. 3A-3D, for example, as well as other suitable shapes. The formation of the sound attenuating portion may include activating the overcoat layer with heat, as indicated in block 546. Other processing steps may also be applied, as indicated in block 548. For example, the outer layer may undergo some curing.

Earplugs and methods of manufacturing earplugs described herein provides several benefits. The earplug described herein may be comfortably positioned in the ear canal of a user to provide a desired level of hearing protection, and the presence of a stiffer elongate core promotes hygiene by eliminating the need to roll down a sound attenuating portion prior to insertion. The method described herein allows an earplug with an internal channel to be efficiently manufactured. An earplug having an outer layer bonded, directly or indirectly, to an elongate core as described herein eliminates the cost and complexity of an additional step of joining a rigid component to a sound attenuating component required of many prior push-in type earplugs. The elongate core and outer layer can be thermally bonded without the need for an additional adhesive or additional assembly step.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures. Any feature or characteristic described with respect to any of the above embodiments can be incorporated individually or in combination with any other feature or characteristic, and are presented in the above order and combinations for clarity only.

EMBODIMENTS

Embodiment 1 is a push-in earplug. The push-in earplug has an elongate core comprising a core material. The push-in earplug also has an outer layer comprising a foam material, the outer layer covering at least a portion of an outer surface of the elongate core. The push-in earplug also has a channel extending through the elongate core from a first end of the elongate core to the second end of the elongate core.

Embodiment 2 includes the features of Embodiment 1, however the foam material comprises a foaming agent that, once activated, increased a volume of outer layer to form a shape of the push-in earplug.

Embodiment 3 includes the features of any of Embodiments 1-2, however the channel has a substantially uniform cross-section extending from the first end of the elongate core to the second end of the elongate core.

Embodiment 4 includes the features of Embodiment 2, however the foaming agent includes an unactivated expandable sphere foaming agent.

Embodiment 5 includes the features of Embodiment 2, however the foaming agent includes unactivated chemical foaming agent.

Embodiment 6 includes the features of Embodiment 2, however the foaming agent is heat activated.

Embodiment 7 includes the features of Embodiment 6, however the foaming agent is heat activated at a temperature that is less than a melting temperature of the core material.

Embodiment 8 includes the features of Embodiment 7, however the foaming agent at least partially bonds to the core material.

Embodiment 9 includes the features of any of Embodiments 1-8, however the elongate core has a first stiffness and the outer layer has a second stiffness. The first stiffness is greater than the second stiffness.

Embodiment 10 includes the features of any of Embodiments 1-9, however the core material includes polyamide.

Embodiment 11 includes the features of any of Embodiments 1-10, however the core material is a blend of materials.

Embodiment 12 includes the features of any of Embodiments 1-11, however the core material also includes an impact modifier.

Embodiment 13 includes the features of Embodiment 12, however the impact modifier includes styrene-ethylene-butylene-styrene.

Embodiment 14 includes the features of any of Embodiments 1-13, however the core material is co-extruded over a channel forming mechanism. The channel forming mechanism is substantially chemically inert with respect to the first material.

Embodiment 15 includes the features of any of Embodiments 1-14, however the outer layer is extruded over the elongate core.

Embodiment 16 is a push-in earplug preform. The pre-form has a channel forming mechanism with a first end and a second end. The preform also has a core material layer, extending substantially from the first end to the second end. The core material substantially covers an exterior of the channel forming mechanism. The pre-form also has an outer layer, extending substantially from the first end to the second end. The outer layer substantially covers an exterior of the core material layer. The outer layer includes a foamable material configured to expand.

Embodiment 17 includes the features of Embodiment 16, however the channel forming mechanism includes a material that is substantially chemically inert with respect to the core material layer.

Embodiment 18 includes the features of any of Embodiments 16-17, however the channel forming mechanism includes a material with a melting point above 190° C.

Embodiment 19 includes the features of any of Embodiments 16-18, however the channel forming mechanism includes a fluoropolymer.

Embodiment 20 includes the features of Embodiment 19, however the channel forming mechanism includes PTFE.

Embodiment 21 includes the features of Embodiment 19, however the channel forming mechanism includes FEP.

Embodiment 22 includes the features of any of embodiments 16-21, however the channel forming mechanism has a circular cross section.

Embodiment 23 includes the features of any of Embodiments 16-22, however the foamable material is configured to expand at an activation temperature. The activation temperature is below a melting point of the channel forming mechanism.

Embodiment 24 includes the features of any of Embodiments 16-23, however the foamable material is configured to expand at an activation temperature. The activation temperature is below a melting point of the core material layer.

Embodiment 25 includes the features of Embodiment 24, however the core material layer includes a mixture of a first material and a second material.

Embodiment 26 includes the features of Embodiment 25, however the foaming agent is heat activated at a temperature that allows for thermal bonding with the second material. The temperature is less than a melting temperature of the first material.

Embodiment 27 includes the features of any of Embodiments 16-26, however the elongate core has a first stiffness and the outer layer has a second stiffness. The first stiffness is greater than the second stiffness.

Embodiment 28 includes the features of Embodiment 27, however the core material includes polyamide.

Embodiment 29 includes the features of any of Embodiments 16-28, however the core material layer also includes an impact modifier.

Embodiment 30 includes the features of Embodiment 29, however the impact modifier includes styrene-ethylene-butylene-styrene.

Embodiment 31 includes the features of any of Embodiments 16-30, however the core material layer is extruded over the channel forming mechanism.

Embodiment 32 includes the features of any of Embodiments 16-30, however the outer layer is extruded over the core material layer.

Embodiment 33 includes the features of any of Embodiments 16-30, however the outer layer is laminated over the core material layer.

Embodiment 34 includes the features of any of Embodiments 16-30, however the outer layer is molded over the core material layer.

Embodiment 35 includes the features of any of Embodiments 16-30, however the outer layer is sprayed onto the core material layer.

Embodiment 36 includes the features of any of Embodiments 16-30, however the outer layer is applied to the core material layer by a dipping process.

Embodiment 37 is a personal protective article. The personal protective article includes a hollow substrate comprising a first material. The personal protective article also includes an outer layer comprising a second material. The outer layer at least partially covers an outer surface of the substrate. The second material includes an activatable foaming agent.

Embodiment 38 includes the features of Embodiment 37, however the second material is configured to at least partially bond to the first material when the activatable foaming agent is activated.

Embodiment 39 includes the features of any of Embodiments 37-38, however the hollow substrate has a substantially uniform cross-section extending from a first end of the hollow substrate to a second end of the hollow substrate.

Embodiment 40 includes the features of Embodiment 39, however the cross-section is selected from the group consisting of: a circle, an oval, a square and a rectangle.

Embodiment 41 includes the features of any of Embodiments 37-40, however the article is an earplug.

Embodiment 42 includes the features of any of Embodiments 37-41, however the foaming agent is configured to expand during activation.

Embodiment 43 includes the features of Embodiment 42, however the foaming agent is configured to expand to take the shape of a mold during activation.

Embodiment 44 includes the features of any of Embodiments 37-43, however the first material includes polyamide.

Embodiment 45 includes the features of Embodiment 44, however the first material also includes an impact modifier.

Embodiment 46 includes the features of Embodiment 45, however the impact modifier is styrene-ethylene-butylene-styrene.

Embodiment 47 includes the features of any of Embodiments 37-46, however the third material is extruded over the substrate.

Embodiment 48 is a method of manufacturing an earplug. The method includes forming an earplug preform with a first end and a second end opposite the first end portion, the earplug preform comprising a substrate covered by a core layer and an outer layer. The substrate is chemical inert with respect to a core material. The method also includes positioning the earplug preform at least partially within a mold cavity. The method also includes applying heat to at least a portion of the mold cavity such that at least a portion of the outer layer expands and conforms to a shape of the mold cavity and the outer layer thermally bonds to the core layer. The method also includes removing the substrate. After the substrate is removed, the core layer has a channel extending from the first end to the second end.

Embodiment 49 includes the features of Embodiment 48, however the mold cavity includes a stem portion and a sound attenuating portion. Applying heat causes the earplug preform to form a stem and a sound-attenuating portion in the stem and sound attenuating portions, respectively.

Embodiment 50 includes the features of any of Embodiments 48-49, however the substrate has a higher melting point than an activation temperature of the second material.

Embodiment 51 includes the features of Embodiment 50, however the substrate substantial maintains a shape during the application of heat.

Embodiment 52 includes the features of any of Embodiments 48-51, however the channel has a substantially constant cross section from the first end to the second end.

Embodiment 53 includes the features of any of Embodiments 48-52, however the substrate includes a fluoropolymer.

Embodiment 54 includes the features of any of Embodiments 48-53, however the substrate includes PTFE.

Embodiments 55 includes the features of any of Embodiments 48-54, however the substrate includes FEP.

Embodiment 56 includes the features of any of Embodiments 48-55, however the outer layer has an activated length. The activated length is longer than a preform length extending from the first end to the second end.

Embodiment 57 includes the features of any of Embodiments 48-56, however applying heat includes subjecting the portion of the outer layer to a temperature of between 100° C. to 205° C.

Embodiment 58 includes the features of any of Embodiments 48-57, however thermal bonding includes the outer layer bonding at least partially to the core material layer.

Embodiment 59 includes the features of any of Embodiments 48-58, however the second material includes unactivated chemical foaming agent.

Embodiment 60 includes the features of any of Embodiments 48-59, however the core material includes polyamide.

Embodiment 61 includes the features of any of Embodiments 48-60, however the core material includes an impact modifier.

Embodiment 62 includes the features of any of Embodiments 48-61, however the core material includes polypropylene.

Embodiment 63 includes the features of any of Embodiments 48-62, however the outer layer of the earplug has a first length, the core layer has a second length. The first length is longer than the second length.

Embodiment 64 includes the features of any of Embodiments 48-63, however an axial length of the core material layer and an axial length of the substrate are about the same.

Embodiment 65 is a method of making an article. The method includes covering a substrate with a core layer. The substrate includes a first end and a second end, and the core layer substantially covers an outer surface of the substrate. The method also includes covering the core layer with an outer layer to prepare a preform having a first end portion and a second end portion, the outer layer includes an expandable material having an activation temperature. The substrate includes a material with a melting point above the activation temperature. The method also includes positioning the first end portion of the preform in a first cavity of a mold and the second end portion in a second cavity of the mold, the first mold cavity having a diameter that is smaller than a diameter of the second mold cavity at its widest point. The method also includes increasing the temperature of the mold cavity to at least the activation temperature of the foaming agent to activate the foaming agent within the second end portion to form the second end portion into a sound-attenuating portion.

Embodiment 66 includes the features of Embodiment 65, however it also includes removing the substrate to create a channel extending through the core layer from the first end to the second end.

Embodiment 67 includes the features of any of Embodiments 65-66, however the substrate is chemically inert with respect to the core layer.

Embodiment 68 includes the features of any of Embodiments 65-67, however the substrate has a constant cross-section from the first end to the second end.

Embodiment 69 includes the features of Embodiment 68, however the cross-section is selected from a group consisting of: a circle, an oval, a square and a rectangle.

Embodiment 70 includes the features of any of Embodiments 65-69, however the substrate has a melting point higher than about 190° C.

Embodiment 71 includes the features of any of Embodiments 65-70, however the substrate includes a fluoropolymer.

Embodiment 72 includes the features of Embodiment 71, however the substrate includes PTFE.

Embodiment 73 includes the features of Embodiment 71, however the substrate includes FEP.

Embodiment 74 includes the features of any of Embodiments 65-73, however the core layer includes polyamide.

Embodiment 75 includes the features of Embodiment 74, however the core layer also includes an impact modifier.

Embodiment 76 includes the features of Embodiment 74, however the core layer also includes a polyolefin.

Embodiment 77 includes the features of any of Embodiments 65-76, however covering the substrate includes extruding the core layer over the substrate.

Embodiment 78 includes the features of any of Embodiments 65-77, however the activation temperature is high enough for thermal bonding between the polyolefin and the expandable material.

Embodiment 79 includes the features of any of Embodiments 65-78, however the activation temperature is between 100° C. and 205° C.

Embodiment 80 is a method of forming an earplug. The method includes forming a core layer with a first end and a second end. The core layer has a hollow interior extending from the first end to the second end. The method also includes covering the core layer with an expandable outer layer. The method also includes activating the expandable outer layer. Activating the expandable outer layer includes causing the expandable outer layer to expand and form a sound attenuating portion and a stem portion. A density of the earplug is greater at the first end than the second end. The hollow interior of the core layer is maintained during activation of the outer layer such that the earplug has a channel extending from the first end to the second end.

Embodiment 81 includes the features of Embodiment 80, however the core layer is formed around a mandrel. Forming includes any of extruding the core layer over the mandrel; laminating the core layer over the mandrel; dipping the mandrel into a core layer material; spraying a core layer material over the mandrel; or molding the core layer over the mandrel.

Embodiment 82 includes the features of Embodiment 81, however the mandrel includes a fluoropolymer.

Embodiment 83 includes the features of Embodiment 82, however the mandrel includes PTFE.

Embodiment 84 includes the features of Embodiment 82, however the mandrel includes FEP.

Embodiment 85 includes the features of Embodiment 81, however the mandrel is chemically inert with respect to the core layer.

Embodiment 86 includes the features of Embodiment 81, however activation includes heating the expandable outer layer to an activation temperature. A melting point of the mandrel is higher than the activation temperature.

Embodiment 87 includes the features of any of Embodiments 80-86, however the core layer is extruded.

Embodiment 88 includes the features of Embodiment 86, however the core layer has a melting point that is higher than an activation temperature of the expandable outer layer.

Embodiment 89 includes the features of Embodiment 86, however the core layer maintains the hollow extending from the first end to the second end throughout the activation of the expandable outer layer.

Embodiment 90 includes the features of Embodiment 86, however the core layer has a melting point higher than 190° C.

Examples

Example 1

Figure 9A:
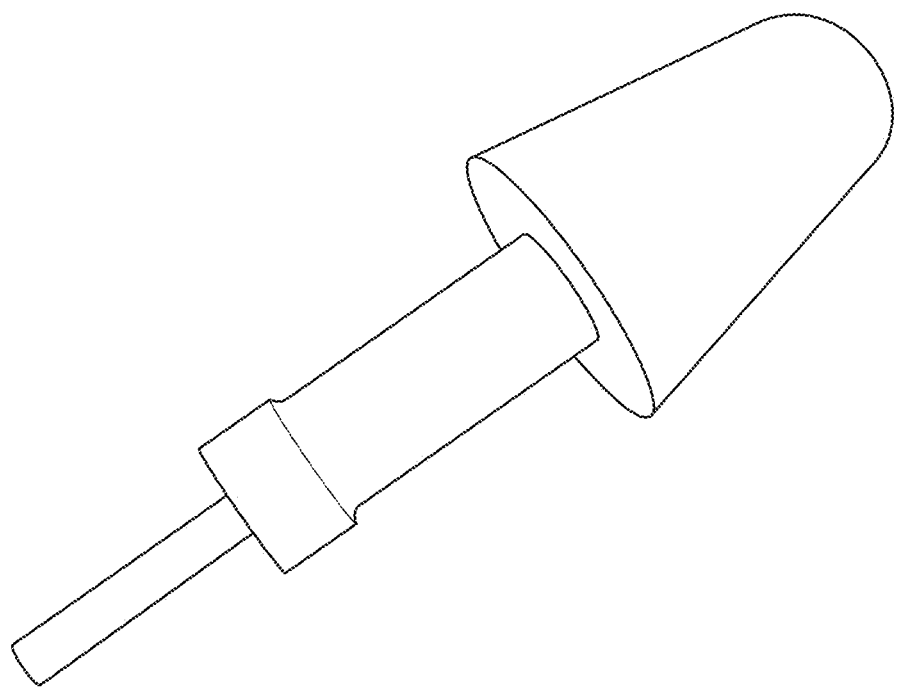
FIGS. 9A-9B illustrate earplugs as described in the Examples.

A one inch cylindrical preforms were made by extruding foamable material over a polypropylene core, then cutting the resultant overcoat extrudate to one inch lengths. A PTFE mandrel, 1.5 mm diameter×30 mm long was inserted into the core. The preform and mandrel was placed in a mold at 375 F for 5 minutes, then cooled to yield an earplug. The mandrel was then easily removed from the finished earplug as shown in FIG. 9A.

Example 2

Figure 9B:
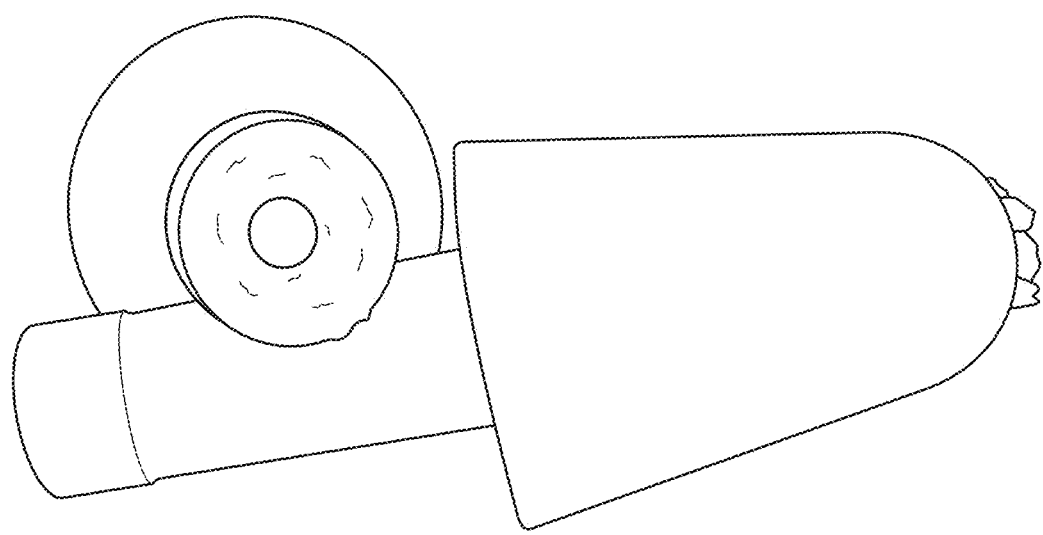

A one inch cylindrical preform was made as in Example 1. An FEP mandrel, 1.5 mm diameter×30 mm long was inserted into the core. The preform and mandrel was placed in a mold at 375 F for 5 minutes, then cooled to yield an earplug. The mandrel was then easily removed o give the finished earplug as shown in FIG. 9B.

What is claimed is:

1. A method of manufacturing an earplug, the method comprising:
 forming an earplug preform with a first end and a second end opposite the first end portion, the earplug preform comprising a substrate covered by a core layer and an outer layer, wherein the substrate is chemically inert with respect to a core material, and wherein the core material comprises a polyamide mixture comprising a polyamide and an impact modifier;
 positioning the earplug preform at least partially within a mold cavity; and
 applying heat to at least a portion of the mold cavity such that at least a portion of the outer layer expands and conforms to a shape of the mold cavity and the outer layer thermally bonds to the core layer; and
 removing the substrate, wherein, after the substrate is removed, the core layer has a channel extending from the first end to the second end.

2. The method of claim 1, wherein the mold cavity comprises a stem portion and a sound attenuating portion, and wherein applying heat causes the earplug preform to form a stem and a sound-attenuating portion in the stem and sound attenuating portions, respectively.

3. The method of claim 1, wherein the substrate has a higher melting point than an activation temperature of a material forming the outer layer.

4. The method of claim 1, wherein the substrate comprises a fluoropolymer.

5. The method of claim 1, wherein the outer layer of the earplug has a first length, the core layer has a second length, and wherein the first length is longer than the second length.

6. The method of claim 1, wherein an axial length of the core layer and an axial length of the substrate are about the same.

7. The method of claim 1, wherein the core material also comprises polypropylene.

8. A method of making an article, the method comprising:
 covering a substrate with a core layer, wherein the substrate comprises a first end and a second end, and the core layer substantially covers an outer surface of the substrate, and wherein the core layer comprises a mixture of a polyamide and an impact modifier;
 covering the core layer with an outer layer to prepare a preform having a first end portion and a second end portion, the outer layer comprises an expandable material having an activation temperature, and wherein the substrate comprises a material with a melting point above the activation temperature;
 positioning the first end portion of the preform in a first cavity of a mold and the second end portion in a second cavity of the mold, the first mold cavity having a diameter that is smaller than a diameter of the second mold cavity at its widest point; and increasing the temperature of the mold to at least the activation temperature of the expandable material to activate the expandable material within the second end portion to form the second end portion into a sound-attenuating portion.

9. The method of claim 8, and further comprising: removing the substrate to create a channel extending through the core layer from the first end to the second end.

10. The method of claim 8, wherein the substrate has a constant cross-section from the first end to the second end.

11. The method of claim 10, wherein the cross-section is selected from a group consisting of: a circle, an oval, a square and a rectangle.

12. The method of claim 8, wherein the substrate has a melting point higher than 190° C.

13. The method of claim 8, wherein covering the substrate comprises extruding the core layer over the substrate.

14. The method of claim 8, wherein the activation temperature is between 100° C. and 205° C.

15. A method of forming an earplug, the method comprising:

forming a core layer with a first end and a second end, wherein the core layer has a hollow interior extending from the first end to the second end, and wherein the core layer is formed around a mandrel, and wherein forming comprises: extruding the core layer over the mandrel; laminating the core layer over the mandrel; dipping the mandrel into a core layer material; spraying a core layer material over the mandrel; or molding the core layer over the mandrel;

covering the core layer with an expandable outer layer; activating the expandable outer layer, wherein activating the expandable outer layer comprises causing the expandable outer layer to expand and form a sound attenuating portion and a stem portion, and wherein a density of the earplug is greater at the first end than the second end; and wherein the hollow interior of the core layer is maintained during activation of the outer layer such that the earplug has a channel extending from the first end to the second end; and wherein the core layer comprises a mixture of a polyamide and an impact modifier.

16. The method of claim 15, wherein the mandrel is chemically inert with respect to the core layer.

17. The method of claim 15, wherein activation comprises heating the expandable outer layer to an activation temperature, and wherein a melting point of the mandrel is higher than the activation temperature.

18. The method of claim 15, wherein the core layer is extruded.

19. The method of claim 15, wherein the core layer has a melting point that is higher than an activation temperature of the expandable outer layer.

20. The method of claim 15, wherein the core layer maintains the hollow interior extending from the first end to the second end throughout the activation of the expandable outer layer.

* * * * *